(12) United States Patent
Bays et al.

(10) Patent No.: US 7,776,594 B2
(45) Date of Patent: Aug. 17, 2010

(54) BONE MARROW INFUSION CHAMBER AND METHOD

(75) Inventors: F. Barry Bays, Collierville, TN (US); Brian R. Harris, Cordova, TN (US)

(73) Assignee: Wright Medical Technology, Inc., Arlington, TN (US)

(*) Notice: Subject to any disclaimer, the term of this patent is extended or adjusted under 35 U.S.C. 154(b) by 1294 days.

(21) Appl. No.: 10/682,289

(22) Filed: Oct. 9, 2003

(65) Prior Publication Data

US 2004/0071668 A1 Apr. 15, 2004

Related U.S. Application Data

(60) Provisional application No. 60/418,077, filed on Oct. 10, 2002.

(51) Int. Cl.
*C12M 3/00* (2006.01)
*C12M 3/06* (2006.01)
*C12N 5/071* (2010.01)

(52) U.S. Cl. .................. 435/372; 435/383; 424/400; 424/422

(58) Field of Classification Search .............. 424/400, 424/422; 435/383, 281.3, 372
See application file for complete search history.

(56) References Cited

U.S. PATENT DOCUMENTS

| | | | |
|---|---|---|---|
| 2,857,913 A | 10/1958 | Miskel | |
| 4,061,143 A | 12/1977 | Ishikawa | |
| 4,366,822 A | 1/1983 | Altshuler | |
| 4,846,174 A * | 7/1989 | Willard et al. | 606/194 |
| 4,911,641 A | 3/1990 | Detsch | |
| 5,197,985 A | 3/1993 | Caplan | |
| 5,269,785 A | 12/1993 | Bonutti | |
| 5,330,357 A | 7/1994 | Keller | |
| 5,618,273 A | 4/1997 | Fischer | |
| 5,824,084 A * | 10/1998 | Muschler | 128/898 |
| 5,824,087 A | 10/1998 | Aspden et al. | |
| 5,997,582 A | 12/1999 | Weiss | |
| 6,049,026 A | 4/2000 | Muschler | |
| 6,554,803 B1 | 4/2003 | Ashman | |
| 6,723,131 B2 | 4/2004 | Muschler | |
| 6,736,799 B1 * | 5/2004 | Erbe et al. | 604/181 |
| 2003/0036762 A1 | 2/2003 | Kerr et al. | |
| 2003/0180262 A1 | 9/2003 | Wironan et al. | |

FOREIGN PATENT DOCUMENTS

| | | |
|---|---|---|
| EP | 1093767 A1 | 4/2001 |
| WO | WO98/16268 A2 | 4/1998 |
| WO | WO98/16268 A3 | 7/1998 |
| WO | WO01/47571 A2 | 7/2001 |
| WO | WO01/47571 A3 | 7/2001 |
| WO | WO02/58762 A2 | 8/2002 |

OTHER PUBLICATIONS

Goshima, et al., The Origin of Bone Formed inComposite Grafts of Porous Calcium Sulfate Ceramic Loaded with Marrow Cells. Clin. Orthop. Rel. Res. 269: 274-283 (1991).

* cited by examiner

*Primary Examiner*—Ruth A Davis

(57) ABSTRACT

A method and apparatus for preparing a bone graft composite using an infusion chamber. A modular tube having a porous material contained therein and having removable end caps is provided. Bone marrow aspirate or other bone morphogenic protein containing suspensions may be infused into the tube. A filter on one end of the tube prevents the fluid from escaping while permitting air to be expelled from the tube as it is filled with bone marrow aspirate. Once infused into the tube, the bone marrow aspirate is allowed to settle to a putty or paste-like consistency, the putty and material together forming a bone graft composite.

22 Claims, 6 Drawing Sheets

BONE MARROW INFUSION CHAMBER AND METHOD

RELATED APPLICATIONS

This application claims priority to U.S. Provisional Patent Application Ser. No. 60/418,077, filed Oct. 10, 2002.

FIELD OF THE INVENTION

The present invention relates to a method and apparatus for producing a bone graft composite. More specifically, the present invention relates to a method and apparatus for producing a bone graft composite using a patient's own bone marrow aspirate or other fluid. BACKGROUND OF THE INVENTION BONE GRAFTING. Bone grafting is a surgical procedure by which bone or a replacement material is placed into spaces between or around bone fractures or defects to aid in healing. It can be used to repair bone fractures that are extremely complex, pose a significant risk to the patient, or fail to heal properly. Specifically, bone grafting is used to help fusion between vertebrae, correct deformities, or provide structural support for fractures of the spine. In addition to fracture repair, bone graft is used to repair defects in bone caused by birth defects, to treat traumatic injury, for bone-void filling in tumor surgery, to treat non-unions, to otherwise induce two opposing bony surfaces to grow together (arthrodesis), or in surgery for bone cancer. Adding bone graft to a surgical site can prompt a biological bone growth response that can result in replacement of bone, correction of bone, or growth of non-anatomical bone. The number of bone graft operations, and the resulting demand for bone graft material, is rapidly increasing.

BONE COMPOSITION. Bone is composed of a soft organic framework or matrix, comprising approximately 90% collagen (synthesized by osteoblasts). The second most abundant protein in the matrix is osteocalcin. Calcium and phosphate deposits surround and support the organic bone matrix. This combination provides bone with some flexibility, as well as strength and rigidity enabling the skeleton to support the body's weight. Within and around the bone matrix are four type of bone cells: osteoblasts, osteocytes, osteoclasts and bone lining cells. Osteoblasts produce the bone matrix. Osteocytes are mature osteoblasts and serve to maintain the bone. Osteoclasts break down and remove bone tissue. Bone lining cells cover bone surfaces. Together, these four types of cells are responsible for building, maintaining and remodeling the bone matrix.

Bone is constantly being remodeled throughout life. There is coordination of bone resorption by osteoclasts and new bone matrix formation by osteoblasts, so that total bone mass remains approximately constant. Resorption occurs when enzymes are released by activated osteoclasts that degrade the bone matrix. Resorption by osteoclasts leaves small cavities in the bone. Osteoblasts line the cavities with a network of soft fibers that become hardened by mineral deposits, such as calcium, to start the growth of new bone. In healthy bone, the remodeling process is in cycles to maintain the normal form, density, and strength of the bone. Loss of bone is due to imbalance between resorption and formation; either excess resorption and/or deficient formation.

In many metabolic diseases of bone there is altered bone turnover, resulting in formation of abnormal bone (for example, Paget's disease), or in bone loss (for example, osteoporosis). Both of these situations can lead to fractures.

QUALITIES OF AN EFFECTIVE BONE GRAFT. There are three ways in which a bone graft can help repair a defect: osteogenesis, osteoinduction, and osteoconduction. Osteogenesis is the formation of new bone by the cells contained within the graft. Graft osteogenesis relates to the cellular elements within a donor graft, which survive transplantation and synthesize new bone at the recipient site. Osteoinduction is a chemical process that elicits mesenchymal stem cells from the surrounding area that differentiate into osteoblasts; molecules contained within the graft (bone morphogenetic proteins (BMPs)) convert the patient's cells into cells that are capable of forming bone. Graft osteoinduction relates to new bone realized through the active recruitment of host mesenchymal stem cells from the surrounding tissue which differentiate into bone-forming osteoblasts. This process is facilitated by the presence of growth factors within the graft, principally bone morphogenetic proteins. Osteoconduction is a physical effect by which the matrix of the graft forms a scaffold on which cells in the recipient are able to form new bone. The scaffold supports the ingrowth of capillaries, perivascular tissues, and osteoprogenitor cells from a host into an implant or graft. Graft osteoconduction refers to the facilitation of blood-vessel incursion and new-bone formation into a defined passive trellis structure.

To function as a suitable bone graft the graft should have a combination of osteoconductive and osteoinductive properties. Preferably, it provides a source of primitive osteoprogenitor cells that form osteoblasts and osteocytes, it produces local growth factors to stimulate bone growth and vascularity in the area, and it acts as a scaffold to bone ingrowth.

TYPES OF BONE GRAFT. There are generally four types of bone grafts used: autografts, allografts, xenografts, and alloplastic grafts.

Autografts, or autologous or autogenous bone, involve bone harvested from a separate site on the patient's body. The area where the bone is harvested from, known as the donor site, is usually the iliac crest region of the hip or a rib. In a typical procedure, bone chips from a patient's pelvic bone are transplanted, or grafted, to the bone graft site (for example, the fracture site). Fresh autogenous cancellous and, to a lesser degree, cortical bone are used for autografts. Autografts incorporate ostegenetic, osteoinductive, and osteoconductive properties, are harvested at both primary and secondary surgical sites, and have no associated risk of viral transmission.

Harvesting bone graft from a patient's body has many disadvantages. The harvest of autogenous bone results in significant cost and morbidity, including scars, blood loss, pain, prolonged operative and rehabilitation time and risk of infection. Furthermore, the availability of autografts is limited and the volume of the graft site can exceed the volume of the available autograft.

Allografts comprise bone harvested from human donors. The patient's body eventually replaces the donor bone with bone natural to the patient. Resorption occurs when enzymes are released by activated osteoblasts that degrade the bone matrix. The advantages of bone allograft harvested from cadaver sources include its ready availability in various shapes and sizes, avoidance of the need to sacrifice host structures and no donor-site morbidity.

The main concern of allografts is their association with transmission of infectious and viral agents. While this concern has been virtually eliminated through donor screening, tissue-processing and sterilization, both freezing and irradiation modify the processes of graft incorporation and affect structural strength.

Xenografts are harvested from animals. The animal bone, most commonly bovine (cow), acts as a filler that the patient's body eventually replaces with natural bone. A synthetic bone graft substitute composed of hydroxyapatite/tricalcium phosphate and pure bovine fibrillar collagen has been developed by Collagraft Corp. and Zimmer, Inc. for mixing with autogenous bone marrow to produce an osteoconductive and osteoinductive substance that acts as a matrix for the bone repair process.

Alloplastic grafts are synthetic materials. Depending on how it they are made, they may be resorbable or non-resorbable. Typically, when not resorbable, the graft acts as a lattice or scaffold upon which natural bone is built. A variety of natural and synthetic replacement materials are used instead of bone. These include collagen; polymers, such as silicone and some acrylics; hydroxyapatite; calcium phosphate; calcium sulfate; ceramics; and resorbable polymeric grafts. Resorbable grafts provide a structure for new bone to grow on. The grafts eventually dissolve, leaving only the new bone behind.

Calcium phosphate cements are typically injectable pastes of calcium and phosphate. After injection, these pastes set firmly with the calcium and phosphate in the paste forming a hard mass of calcium phosphate ceramic. Calcium phosphate ceramic is very similar to hydroxyapatite found in bone. Once set, the ceramic serves as an internal splint, holding the fracture in the position maintained which the cement set. The ceramic is osteoconductive and allows bone forming cells to grow over its surface to form new bone. The ceramic slowly dissolves, allowing new bone to grow into the graft site replacing the graft without weakening the bone.

A bioactive glass implant has been developed by Bioglass US Biomaterials Corp. that reacts with body fluid causing bone-like pores to evolve on the implant surface. Collagen bonds to the surface and new bone forms and fills the space between the implant, collagen fibers and bone. A coralline hydroxyappatite graft has been developed by Interpore-Cross (ProOsteon) that is composed of a sea coral converted by hydrothermal exchange reaction into coralline hydroxyappatite. It acts as a lattice for new bone formation.

Norian has developed a Skeletal Repair System (SRS) comprising a bone mineral substitute of monocalcium and tricalcium phosphate, calcium carbonate, and liquid sodium phosphate. The bone mineral substitute is a paste that hardens to turn into the mineral phase of bone (osteoconductive)and is replaced by bone.

A graft has been developed at MIT consisting of hydroxyapatite and a biodegradable polymer, poly(lactide-co-glycolide) or PLAGA. This polymer is in the form of microspheres averaging 150 microns in diameter and acts as scaffolding for the growth of new bone in the patient. Over time, the PLAGA spheres degrade and are excreted; the tiny holes they leave give the graft a porous structure like natural bone, allowing new bone cells to infiltrate the material.

Bone morphogenetic proteins (BMPs) and transforming growth factor-βs (TGF-βs) are regulators in bone repair and regeneration and have been studied for use in bone grafting. Transforming Growth Factor-Beta One (TGF-βI) is an osteoinductive protein that may be suitable for treating non-unions, bone defects, and in revision implant surgery. Osteogenic Protein-1, also known as also known as Bone Morphogenic Protein-7, is a member of a class of naturally occurring growth factors called Bone Morphogenetic Proteins (BMPs), and stimulates bone formation by causing precursor stem cells to differentiate into bone-forming cells. OP-1Implant, developed by Stryker Biotech, induces new bone formation in both developing and mature skeletal systems. Bone Morphogenic Protein-2 (BMP-2) has also been used for inducing bone growth and repair and may be suitable for trauma, AVN, bone loss from tumors, and spinal reconstruction. Medtronic Sofamor Danek has introduced a form of genetically engineered BMP-2 under the trade name Infuse™.

BONE MARROW AS BONE GRAFT MATERIAL. Naturally derived bone marrow is an effective component of a bone graft material. Bone marrow contains bone morphogenic protein (BMP) and is osteoinductive. The effectiveness of bone marrow may be partially due to the immature bone forming cells that are contained in bone marrow.

A development in bone graft technology involves combining a bone graft substitute with the patient's own bone marrow to reduce bone graft site morbidity and enhance fusion rates. Sulzer Spine-Tech has developed a product, Healos Bone Graft Substitute that is a matrix made up of collagen with hydroxyapatite spun thereupon. Microscopically it resembles bone and it works by absorbing harvested bone marrow before insertion. HealosMP52 is being developed and utilizes BioPharm GmbH's recombinant human growth factor MP52 (also known as BMP14 or rhGDF-5) and Healos Bone Graft Substitute. Other composite materials using synthetic graft materials as carriers for bone marrow cells have also been developed.

Bone matrix gels are a type of graft that is a highly purified gel of osteoconductive human bone matrix and can be combined with bone marrow to provide an osteoconductive scaffold on which bone marrow cells can attach and grow. Demineralized Bone Matrix (DBM) takes the proteins from demineralized bone and adds it to a substrate (e.g. glycerol or a polymer) to produce a mostly osteoinductive product. DBM is typically used as an adjuvant to spinal and joint fusions, repair of osseous defects, and arthroplasties. Wright Medical Technology has developed a DBM composite or formulation with surgical grade calcium sulfate powder and carboxymethylcellulose (CMC), known as AlloMatrix™, produced as an injectable or formable putty. Another injectable paste or putty was developed by GenSci OrthoBiologics and is marketed as OrthoBlast™. OrthoBlast is a heat sensitive copolymer with cancellous bone chips and DBM. Another DBM product, called Grafton™, was developed by Osteotech and is DBM combined with glycerol, produced as a gel.

Some researchers have thought it desirable to increase the relative concentration of connective tissue progenitor cells in composite implants incorporating bone marrow aspirate. The reasoning is that connective tissue progenitor cells, which have the capacity to differentiate into cartilage, bone, and other connective tissue such as fat, muscle, and fibrous tissue are present in the bone marrow in very minute amounts and that a composite implant made, for example, by soaking a given volume of synthetic carrier graft material in a comparable volume of fresh bone marrow contains relatively few connective tissue progenitor cells.

One technique for increasing the relative concentration of connective tissue progenitor cells in composite implants involves plating a suspension of bone marrow cells onto tissue culture dishes, culturing the cells in a select medium for one or more days until the number of connective tissue progenitor cells in the culture increases, and then detaching the cells from the tissue culture dishes to provide a cell suspension containing a culturally-expanded population of connective tissue progenitor cells. Composite implants are then made by soaking synthetic ceramic carriers in this suspension of culturally-expanded cells.

Muschler, in U.S. Pat. Nos. 5,824,084 and 6,049,026 discloses a composite bone graft and method for preparing such. The improved composite bone graft of the Muschler patent purports to include an enriched population of connective tissue progenitor cells and a greater number of connective tissue progenitor cells per unit volume than that found in the original bone marrow aspirate. The bone graft is prepared by providing a bone marrow aspirate suspension and passing the bone marrow aspirate suspension through a porous, biocompatible, implantable substrate resulting in a composite bone graft having an enriched population of connective tissue progenitor cells that collects in an effluent collector separate from the mixing chamber (i.e., container 14).

SUMMARY OF THE INVENTION

The present invention relates to a method and apparatus for preparing a bone graft composite. The invention offers flexibility by allowing the composite to be mixed (i.e., infused) in the operating room, preferably, but not only, using the patient's own healing potential in the form of bone marrow aspirate, blood, or platelet concentrate.

The apparatus comprises a modular tube containing a porous or non-porous, biocompatible, implantable material. The modular tube has first and second ends, first and second end caps being provided for detachably coupling to the first and second ends. The first and second end caps are provided with first and second couplings. The first coupling of each end cap is attachable to the modular tube. The second coupling of each end cap may be attached to a further component. The first and second end caps may be identical or may be alternately configured. In use, the second coupling of the first end cap may be coupled to a syringe and the second coupling of the second end cap may be coupled to a filter. Preferably, the second coupling of both the first and second end caps is configured to mate with a sealing cap such as a luer cap. The exact mechanism by which the end caps are coupled to the tube, the sealing caps, the syringe, or the filter is unimportant. However, it may be useful to provide threadably couple the end caps to the tube and pressfit couple the end caps to the sealing caps, the filter and/or the plunger. Bone marrow aspirate or other fluid may be infused into the tube and around the material through the first end of the tube. The filter on the second end of the tube allows air to be expelled from the tube as it is filled with the bone marrow aspirate. However, the filter should be sufficiently dense to prevent leakage of the bone marrow aspirate.

The material provided within the tube may be any suitable porous or non-porous, biocompatible, implantable material. For instance, the material may comprise grains of calcium sulfate, calcium phosphate, tri-calcium phosphate, hydroxyapatite, coral hydroxyapatite, demineralized bone matrix, mineralized bone matrix, or biopolymers such as, for example, polylactic acid, polyglycolic acid, polygalactic acid, polycaprolactone, polyethylene oxide, polypropylene oxide, polysulfone, polyethylene, polypropylene, or hyaluronic acid, which may be purified with or without crosslinking, bioglass (including silica based resorbable bioglasses) and collagen. The exact configuration of the material within the tube is not of particular importance. Preferably, the material comprises a plurality of small pieces such as pebbles. The material should be sized such that a plurality of pieces within the tube fills the tube but maintains sufficient space around the pieces for the bone marrow to seep around the pieces.

In the preferred method of the present invention, bone marrow aspirate is harvested using a separate syringe and needle. Preferably, the method is performed intraoperatively harvesting the bone marrow aspirate from the patient. After harvesting of the marrow, the needle may be removed from the syringe. The modular tube is then provided having a biocompatible, implantable material within the tube. Preferably, sufficient material is provided inside the tube to fill the inside of the tube but maintain spaces around the individual pieces of material. The modular tube has a first end and a second end. First and second detachable end caps, each, having a first and second coupling, are provided. The first and second detachable end caps are coupled to the first and second ends, respectively, of the tube via the first coupling of each end cap. The second coupling of each end cap is attachable to a further component. The second coupling of the end cap of the first end of the modular tube is coupled to the separate syringe having the harvested bone marrow therein. The second coupling of the second end cap is coupled to a filter. As the plunger of the syringe is depressed, the marrow from the syringe is forced into the tube at its first end, passed over and around the material, and forced towards the second end of the tube as air from the tube escapes through the filter attached to the second coupling of the end cap of the second end of the tube. Furthermore, if the material is porous, the bone marrow aspirate will seep into the pores of the material. The syringe may then be removed from the tube if desired. If the syringe is removed, a sealing cap, such as a luer cap, may be coupled to the second coupling of the first end cap to prevent any leakage of the bone marrow aspirate from the tube. Similarly, the filter may be removed and a sealing cap, such as a luer cap, coupled to the second coupling of the second end cap. Alternately, a sealing cap may be coupled directly to the filter.

The tube is allowed to rest such that the marrow begins to solidify in and around the material within the tube. In the case of porous materials, some marrow will be absorbed thereby. However, the material need not be so porous as to absorb any significant amount of marrow. Rather, the marrow will primarily solidify around the material to form a structure around and including the material. As it solidifies, the marrow will form a putty or paste-like substance. The longer the marrow is allowed to rest, the more firm it will become. Once the desired consistency is achieved, the first and/or second end caps are removed. The putty substance, together with the material that was in the tube, comprises a bone graft composite and is then accessible to the surgeon. It may be desirable to force the bone graft composite from the tube using a plunger to provide a log of material. Alternately, the bone graft composite may be removed piecemeal with, for instance, a scraper.

Additional products may be added directly within the tube or to the material within the tube if desired. These may include, for example, growth factors such as isoforms of platelet derived growth factors (PDGF), fibroblast growth factors, epithelial growth factors, isoforms of transforming growth factor Beta, insulin-like growth factors, and bone morphogenic proteins.

An alternate embodiment of the invention comprises a vacutainer in the place of the tube of the first embodiment. The vacutainer has a closed end and an open end. The open end is sealed with a vacuum seal. A suitable porous, biocompatible, implantable material is provided within the vacutainer. After harvesting of the bone marrow aspirate, the seal is punctured and the bone marrow aspirate is drawn into the vacutainer. The bone marrow aspirate is allowed to rest in the vacutainer. Once the desired consistency is achieved, the seal may be removed to allow the surgeon access to the bone graft composite.

DETAILED DESCRIPTION OF THE PREFERRED EMBODIMENTS

Figure 1:
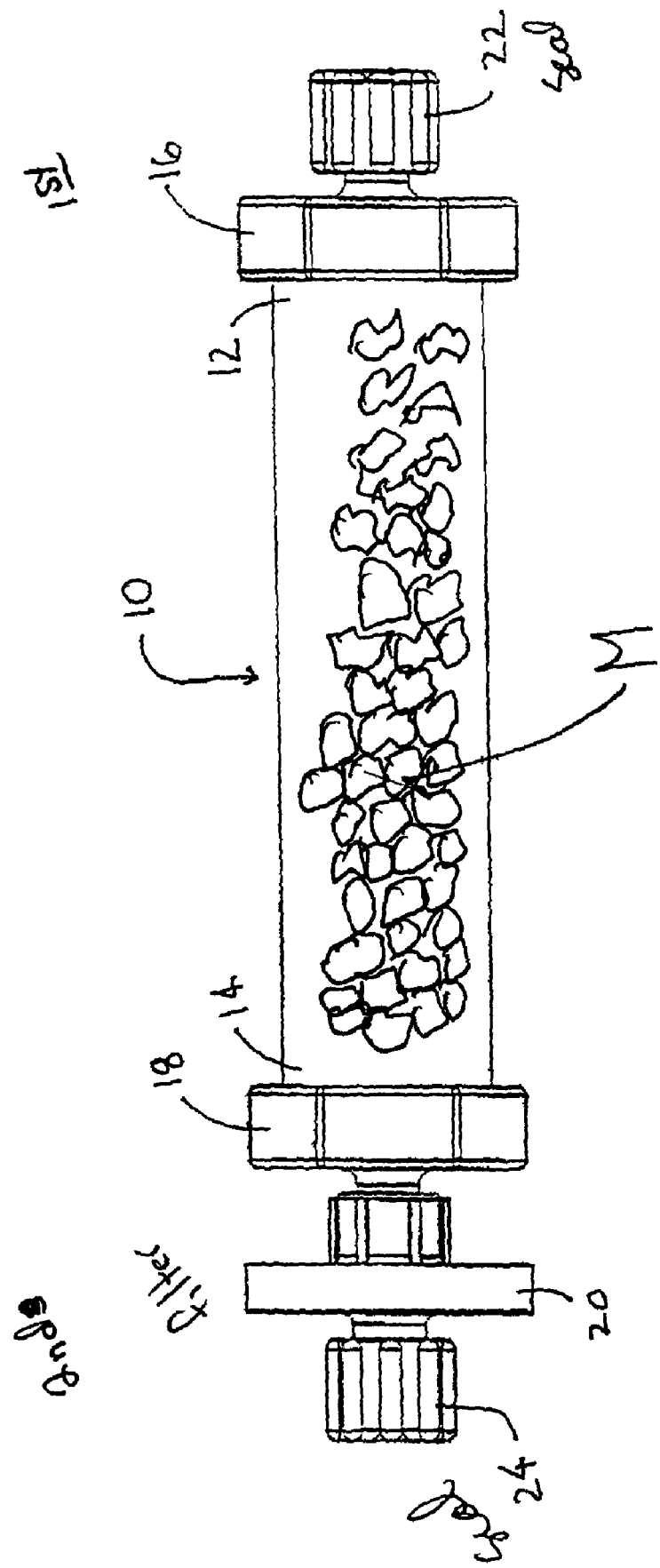
FIG. 1 a perspective view of a first embodiment of the present invention.

The present invention relates to a method and apparatus for preparing a bone graft composite. The invention allows the composite to be mixed (i.e., infused) in the operating room, preferably, but not only, using the patient's own healing potential in the form of bone marrow aspirate, blood or platelet concentrate. Like structures are provided with like reference numerals throughout the drawings.

As seen in FIG. 1, the apparatus comprises a modular tube 10 having first and second ends, 12 and 14. The size of the tube 10 is not of particular importance. However, convenient sizes are 7 cc and 15 cc. Preferably, the tube 10 is manufactured from a material which is biocompatible and pyrogen-free such as glass, plastic or metal. The tube 10 is filled, either partially or completely, with a porous or non-porous, biocompatible, and implantable material M ("the material"). Regardless of the amount of material M in the tube 10, sufficient space should remain in the tube 10 for bone marrow aspirate to be received around the material M in the tube 10. The inside of the tube 10 and the material M should be sterile.

The material M provided within the tube 10 may be any suitable porous or non-porous, biocompatible, implantable material. For instance, the material M may comprise grains of calcium sulfate, calcium phosphate, tri-calcium phosphate, hydroxyapatite, coral hydroxyapatite, demineralized bone matrix, mineralized bone matrix, or biopolymers such as, for example, polylactic acid, polyglycolic acid, polygalactic acid, polycaprolactone, polyethylene oxide, polypropylene oxide, polysulfone, polyethylene, polypropylene, or hyaluronic acid, which may be purified with or without crosslinking, bioglass (including silica based resorbable bioglasses) and collagen. While it is desirable that the material M be porous, biocompatible, implantable, the amount of porosity of the material M is not of particular importance. The exact configuration of the material M within the tube 10 is not of particular importance. Preferably, the material M comprises a plurality of small pieces. The size and shape of the individual pieces of material M should be such that when bone marrow aspirate is introduced into the tube 10, the bone marrow aspirate will fill in gaps between the pieces of material M. Thus, for example, the pieces of material M may be irregularly shaped as small pebbles or chips or regularly shaped as spheres, pellets, or cylinders.

Additional products may be added to the tube 10 or to the material M within the tube 10 if desired. These may include, for example, growth factors such as isoforms of platelet derived growth factors (PDGF), fibroblast growth factors, epithelial growth factors, isoforms of transforming growth factor Beta, insulin-like growth factors, and bone morphogenic proteins.

The first and second end caps 16 and 18 are configured for detachable coupling to the first and second ends 12 and 14 of the tube 10. Each of the first and second end caps 16 and 18 is configured for further attachment to another component after attachment to the tube 10. Specifically, the first end cap 16 may be coupled to a syringe 100 (FIG. 6B) and the second end cap 18 may be coupled to a filter 20. Alternately, the first and second end caps 16 and 18 may be coupled to a sealing cap. First and second sealing caps 22 and 24, such as luer caps, may be provided to seal each of the first and second end caps 16 and 18. The filter 20 should allow air to be expelled from the tube 10 but should be sufficiently dense to prevent leakage of the bone marrow aspirate, as the bone marrow aspirate is introduced into tube 10 at first end 12 and forced towards second end 14 by the action of the plunger of syringe 100.

Figure 2:
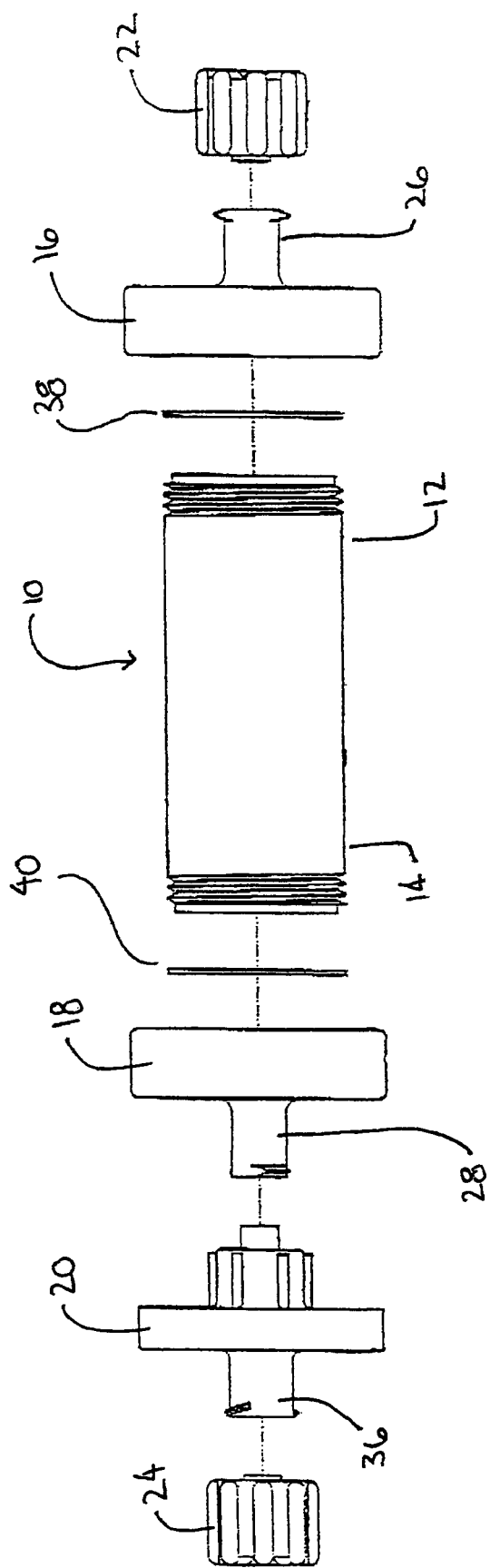
FIG. 2 is an exploded view of a further embodiment of the present invention.

FIG. 2 is an exploded view of one embodiment of the present invention and particularly shows an exemplary coupling mechanism of each of the components. In this embodiment, the first and second ends 12 and 14 of the tube 10 are threaded. Each of the first and second end caps 16 and 18 includes first and second couplings. The first coupling is complimentary threaded to threadably couple with the first and second ends. The second coupling 26 and 28 of the first and second end caps enable further coupling of the end caps to additional components. The second couplings 26 and 28 may be configured as female luer caps. The second coupling of the first end cap may mate with another syringe (not shown) or a sealing cap 22, such as a male luer cap. The second coupling of the second end cap 28 may mate with the filter 20 or a sealing cap 24, such as a male luer cap. The filter 20 may also provided with a coupling 36 for mating with the sealing cap 24. First and second washers 38 and 40 may be provided between the first and second ends 12 and 14 and the first and second end caps 16 and 18 to relieve friction, prevent leakage, or distribute pressure. The washers may be metal, rubber, plastic, or any suitable material.

Figure 3:
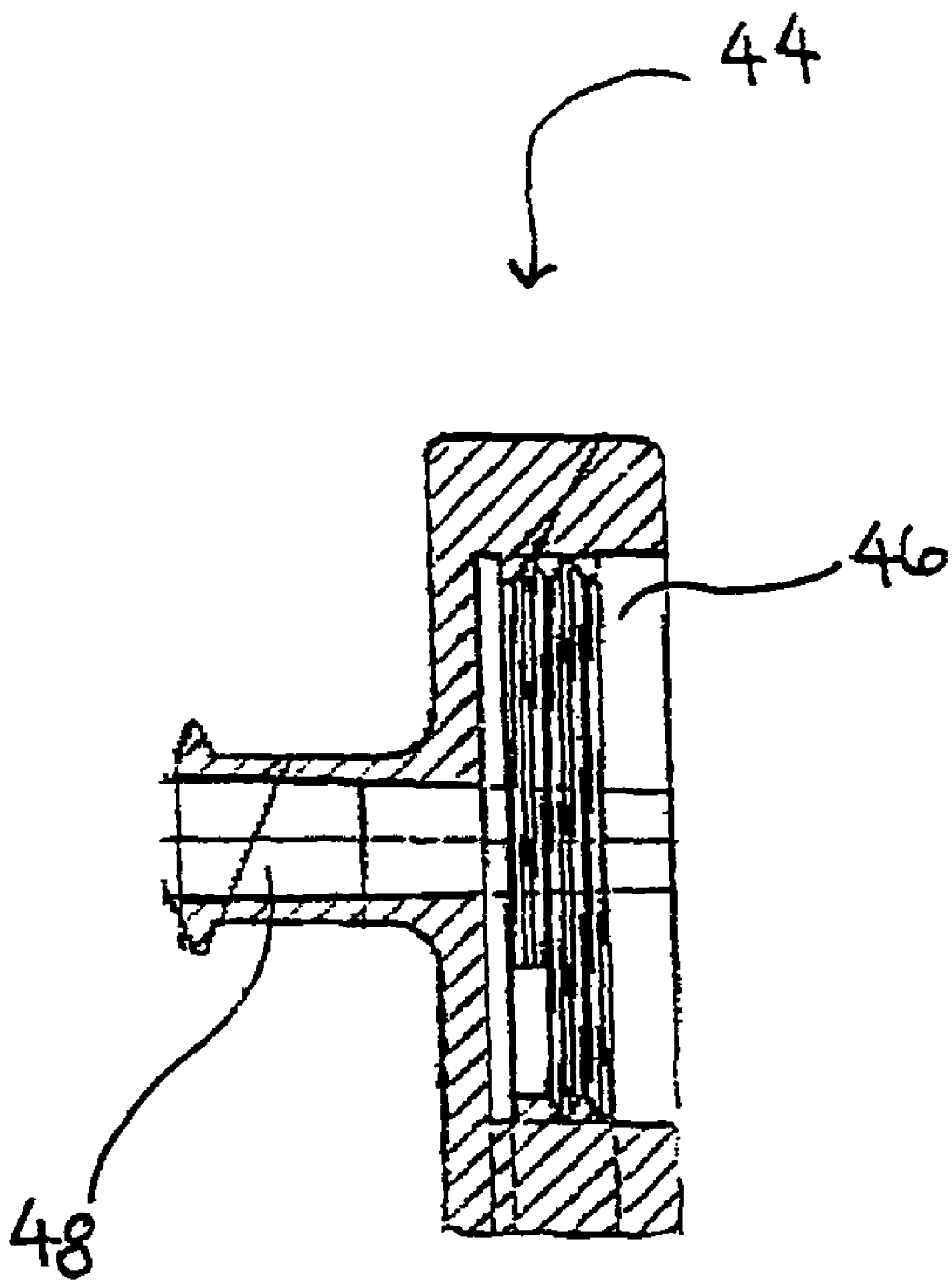
FIG. 3 is a side cross-sectional view of an end cap for use with one embodiment of the present invention.

FIG. 3 illustrates a suitable configuration for an end cap 44 in accordance with the present invention. The end cap 44 may be used as either the first or the second end cap of the apparatus. Further, the first and second end caps may be identical or may differ. The end cap 44 is provided with a first coupling 46 and a second coupling 48. The first coupling 46 is threaded and is designed to mate with threading on the end of the tube 10. The second coupling 48 is a female coupling and is designed to mate with a male coupling on the filter, a sealing cap (such as a luer cap), or a syringe.

Figure 4:
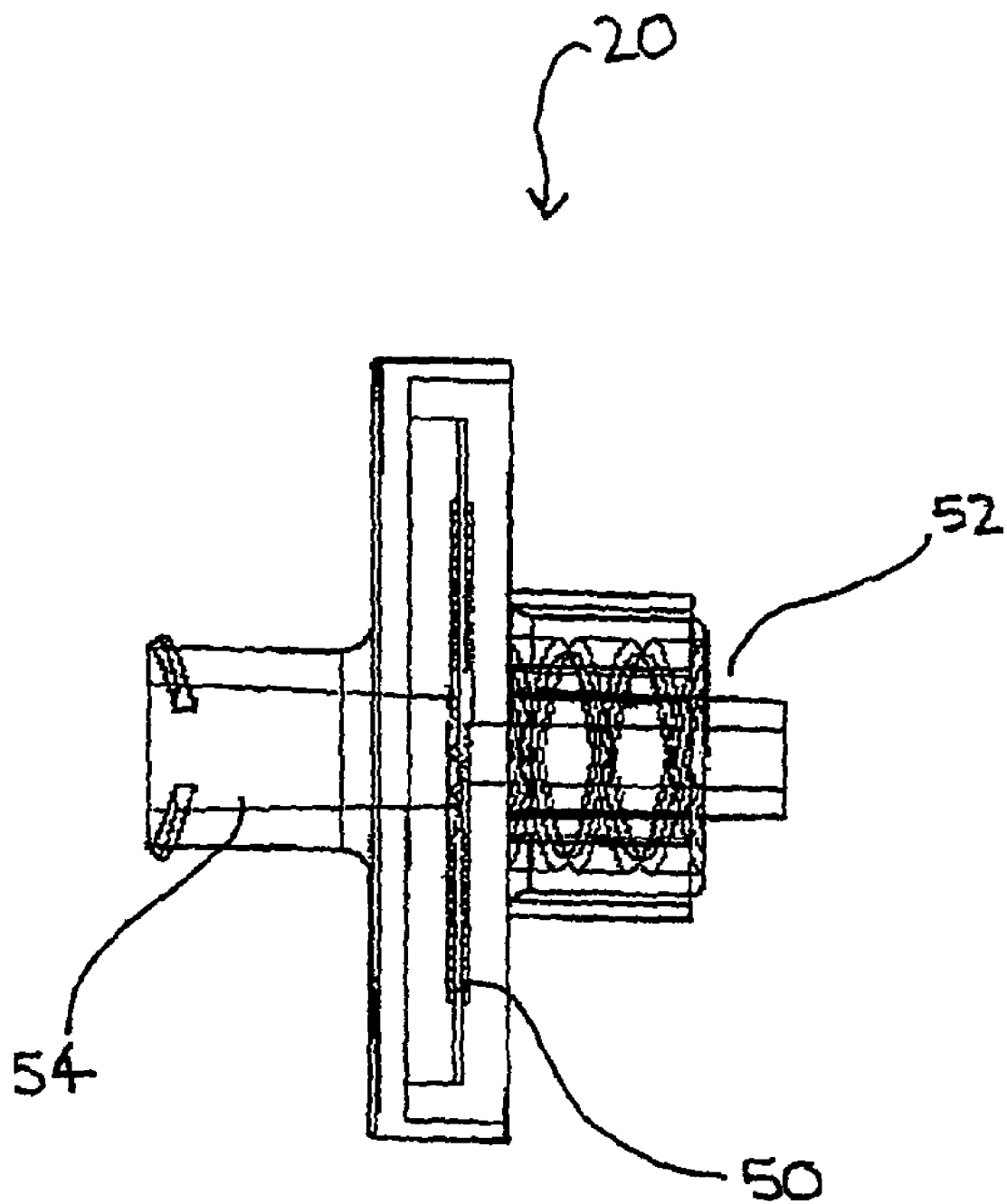
FIG. 4 is a side cross-sectional view of a filter for use with one embodiment of the present invention.

As seen in FIG. 4, a filter 20 for use with the present invention includes a filter component 50 allowing air to be expelled through the filter but preventing seepage of bone marrow aspirate therethrough. The filter is also provided with first and second couplings 52 and 54. The first coupling 52 mates with the second coupling of the second end cap. The first coupling 52 may be provided as a male luer fitting. The second coupling 54 for mating with a sealing cap. It is not necessary for a sealing cap to be coupled to the filter. However, it may be desirable to couple the sealing cap to the filter to provide a relatively air tight environment after the air has been expelled from the tube 10.

Figure 6A:
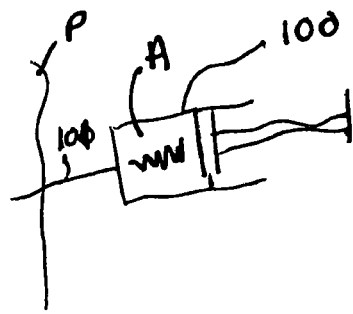
FIGS. 6A and 6B depict the method according to the invention.
Figure 6B:
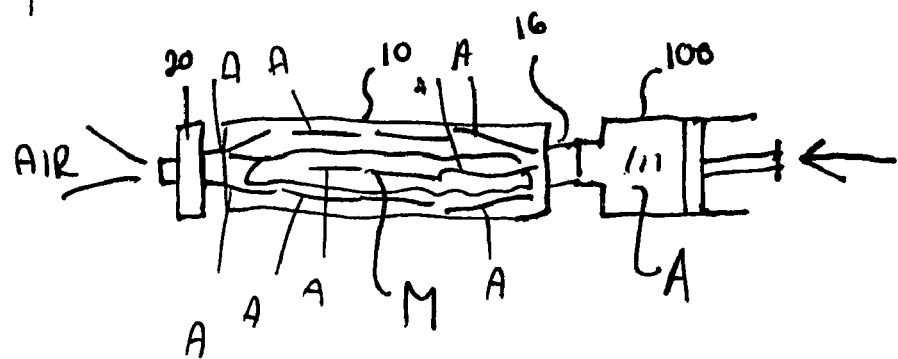

In the preferred method of the present invention, as shown in FIG. 6A, bone marrow aspirate A is harvested in accordance with known methodology using a syringe 100 and needle 101. Preferably, the method is performed intraoperatively, harvesting the bone marrow aspirate A from the patient P. Bone marrow aspirate A contains plasma, nucleated connective tissue progenitor cells, nucleated hematopoietic cells, endothelial cells, and cells derived from contaminating peripheral blood, including red cells and platelets. Since bone marrow aspirate also contains peripheral blood, it may be useful for the bone marrow to be collected in a syringe containing an anti-coagulant. Suitable anti-coagulants include, for example, heparin, sodium citrate, and EDTA.

Figure 7:
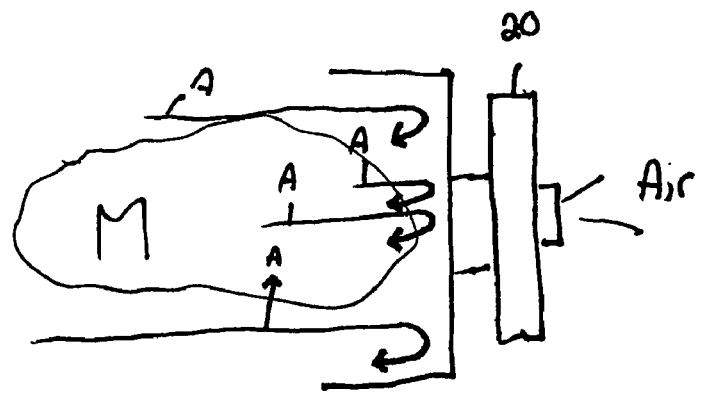
FIG. 7 depicts the flow pattern of bone marrow aspirate at the second end of a tube according to the invention.

After harvesting of the bone marrow aspirate A, the needle 101 may be removed from the syringe 100. The apparatus including the tube 10 having first and second end caps 16 and 18 coupled to the first and second ends 12 and 14 thereof, and a filter 20 coupled to the second end cap is then provided for use with the method. The tube 10 includes a porous, biocompatible, implantable material M, as previously described above. Sufficient material M is provided to fill the inside of the tube 10 but maintain spaces around the individual pieces of material M. The first end cap 16 is then attached to the syringe 100 having the harvested bone marrow aspirate A therein. This may be done by mating the second coupling 26 of the first end cap 16 to the syringe 100. By depressing the plunger of syringe 100, the bone marrow aspirate A from the syringe 100 is forced into the tube 10, air inside the tube 10 escapes through the filter 20 attached to the second end cap 18 of the tube 10, and the bone marrow aspirate A seeps in and around the material M within the tube 10 as the bone marrow aspirate A enters the tube 10 from the first end and is forced towards the second end and then stopped by the porosity of the filter, which is such that the bone marrow aspirate A cannot pass there through. Additionally, as shown in FIG. 7, typically what occurs is that bone marrow aspirate will be forced back towards the first end of tube 10 and thereby even further mix with material M. Furthermore, if the material is porous, the bone marrow aspirate will seep into the pores of the material. Given the porosity of the material M, marrow will seep therein and provide a composite graft. However, the material M need not be so porous as to absorb any significant amount of marrow. The syringe 100 may then be removed from the tube 10 if desired. If the syringe 100 is removed from the tube 10, a sealing cap 32 may be coupled to the first end cap 16 to prevent any leakage of the bone marrow aspirate A from the tube 10. Likewise, once the bone marrow aspirate A is in the tube 10 and air from the tube 10 has been expelled through the filter 20, the filter 20 may be removed from the second end cap 18 and a sealing cap 24 coupled in its place. Alternately, the sealing cap 24 may be coupled directly to the filter 20 or the filter 20 may be left in place without the sealing cap 24 being coupled thereto. If the sealing cap 24 is used, it functions to make the tube 10 relatively airtight after the air has been expelled therefrom.

The tube 10 is allowed to rest such that the marrow begins to solidify in and around the material M within the tube 10. The marrow will primarily solidify around the material M to form a structure around and including the material M. As it solidifies, the marrow will form a putty or paste-like substance. The longer the marrow is allowed to rest, the more firm it will become. Once the desired consistency is achieved, the first and/or second end caps 16 and 18 (and any further components attached thereto) are removed. The putty substance, together with the material M that was in the tube 10, comprises a bone graft composite and is then accessible to the surgeon. It may be desirable to force the bone graft composite from the tube 10 using a plunger (after removing end caps 16, 18) to provide a log of material. Alternately, the bone graft composite may be removed piecemeal with, for instance, a scraper.

The invention has been discussed primarily with respect to the insertion of bone marrow aspirate into tube 10. However, the invention is not so limited. For example, any suspension containing bone morphonegenic proteins may be used, whether naturally derived in the form of bone marrow aspirate or genetically created products.

Furthermore, tube 10 may have inserted therein blood or platelet concentrate, which may be mixed (infused) with material M to create a bone graft having the proper consistency as one created with bone marrow aspirate, but where the need for BMPs is not paramount.

Figure 5:
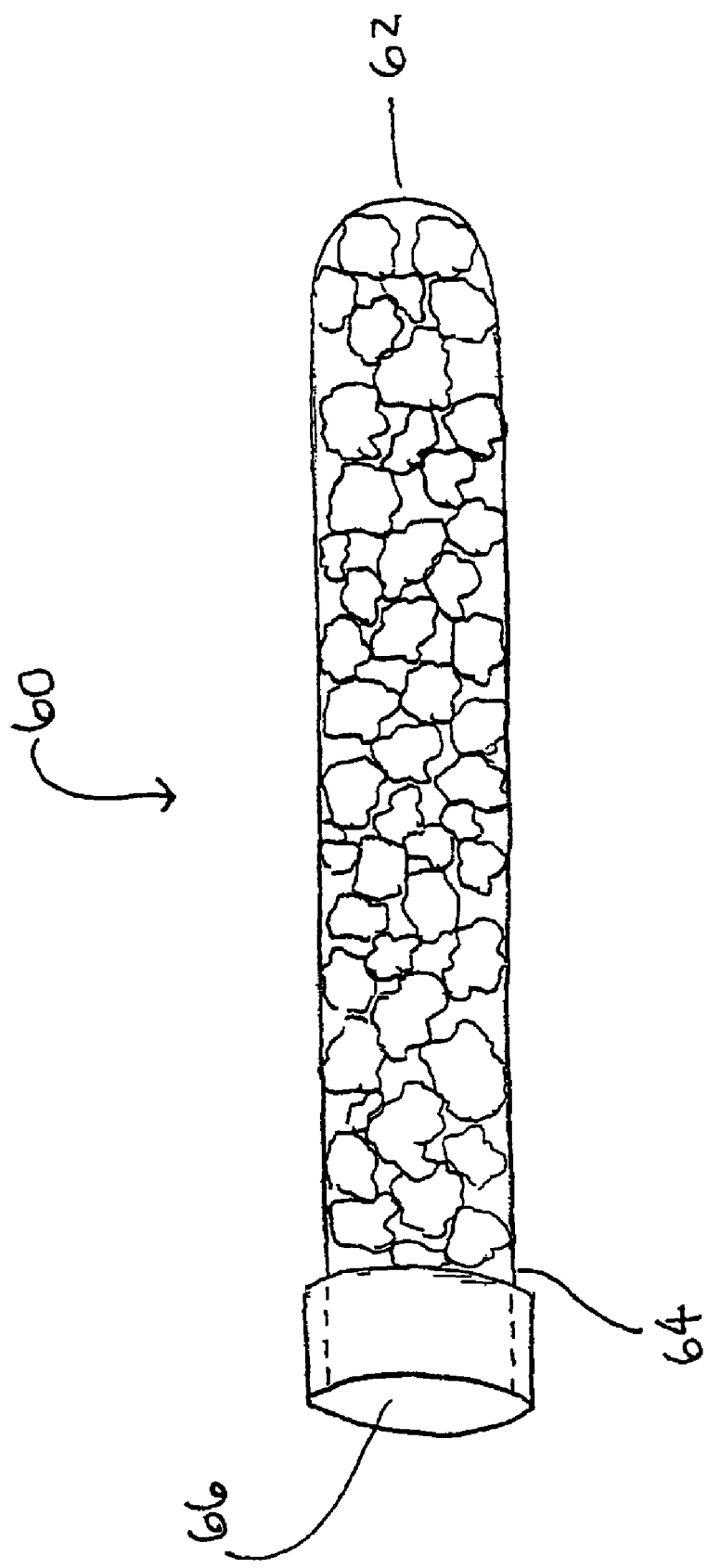
FIG. 5 is a perspective view of another embodiment of the present invention.

An alternate embodiment of the invention is illustrated in FIG. 5 and comprises a vacutainer 60 in the place of the tube 10 of the first embodiment. The vacutainer 60 has a closed end 62 and an open end 64. The open end is sealed with a vacuum seal 66. A suitable porous, biocompatible, implantable material M is provided within the vacutainer 60. After harvesting of the bone marrow aspirate, the seal 66 is punctured and the bone marrow aspirate is drawn into the vacutainer 60. The bone marrow aspirate is allowed to rest in the vacutainer 60. Once the desired consistency is achieved, the seal 66 may be removed to allow the surgeon access to the bone graft composite.

Regardless of the embodiment used, the present invention enables a bone graft composite can be prepared while the patient is in the operating room directly prior to the bone graft placement.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. An apparatus for preparing a bone graft composite comprising a bone graft material and a bone marrow aspirate, the apparatus comprising:
   a tube having a first open end and a second open end;
   a first end cap removably coupled to said first open end, said first end cap having a passage therethrough to allow fluid communication between a bone marrow aspirate delivery member and said tube, a trailing end of said first end cap configured for selective attachment to a bone marrow aspirate delivery member;
   a second end cap removably coupled to said second end, said second end cap having a passage therethrough to allow fluid communication between said tube and a filter, a leading end of said second end cap configured for selective attachment of a filter;
   a filter member removably coupled to said leading end of said second end cap;
   a filter in said filter member, said filter configured to prevent bone marrow aspirate from passing therethrough while permitting air to pass therethrough, said filter in fluid communication with said tube via said passage of said second end cap; and
   a bone graft material in the tube.

2. The apparatus of claim 1, wherein said bone graft material is selected from the group consisting of calcium sulfate, calcium phosphate, tri-calcium phosphate, hydroxyapatite, coral hydroxyapatite, demineralized bone matrix, and mineralized bone matrix.

3. The apparatus of claim 2, further comprising said filter member sealed by a removable second sealing cap on a leading end of said filter member.

4. The apparatus of claim 1, wherein said bone graft material comprises tri-calcium phosphate.

5. The apparatus of claim 4, wherein said bone graft material comprises a plurality of small pieces of bone graft material.

6. The apparatus of claim 5, further comprising a first washer disposed between said first end cap and said first end of said tube, and a second washer disposed between said second end cap and said second end of said tube.

7. The apparatus of claim 6, further comprising said first end cap sealed by a removable first sealing cap on a trailing end of said first end cap.

8. The apparatus of claim 1, wherein said bone graft material is porous to bone marrow aspirate.

9. The apparatus of claim 1, wherein said bone graft material comprises a plurality of small pieces of bone graft material.

10. The apparatus of claim 1, further comprising said first end cap sealed by a removable first sealing cap on a trailing end of said first end cap.

11. The apparatus of claim 10, further comprising said filter member sealed by a removable second sealing cap on a leading end of said filter member.

12. The apparatus of claim 1, further comprising a first washer disposed between said first end cap and said first end of said tube.

13. The apparatus of claim 12, further comprising a second washer disposed between said second end cap and said second end of said tube.

14. The apparatus of claim 1, further comprising bone marrow aspirate in said tube, said bone marrow aspirate having been introduced into said tube through said first end of said tube, and air having been expelled through said filter of said filter member to facilitate introduction of said bone marrow aspirate into said tube.

15. The apparatus of claim 14, wherein said bone marrow aspirate has been allowed to coagulate in said tube while in contact with said bone graft material.

16. The apparatus of claim 14, wherein said bone graft material is substantially saturated with said bone marrow aspirate.

17. The apparatus of claim 14, further comprising coupling a second sealing cap to said filter member to thereby provide a relatively air tight environment after air has been expelled from the tube.

18. The apparatus of claim 14, wherein said bone graft material comprises tri-calcium phosphate.

19. The apparatus of claim 18, further comprising a first washer disposed between said first end cap and said first end of said tube.

20. The apparatus of claim 19, further comprising a second washer disposed between said second end cap and said second end of said tube.

21. The apparatus of claim 20, wherein said trailing end of said first end cap configured for attachment to a bone marrow aspirate delivery member is configured for attachment to a syringe.

22. The apparatus of claim 21, further comprising coupling a second sealing cap to said filter member to thereby provide a relatively air tight environment after air has been expelled from the tube.

* * * * *